United States Patent
Alam et al.

(10) Patent No.: US 6,944,493 B2
(45) Date of Patent: *Sep. 13, 2005

(54) INDOCYANINE GREEN (ICG) COMPOSITIONS AND RELATED METHODS OF USE

(75) Inventors: Abu Alam, Lake Forest, IL (US); Ashok J. Chavan, Bloomington, IL (US); Robert W. Flower, Hunt Valley, MD (US)

(73) Assignee: Akora, Inc., Buffalo Grove, IL (US)

(*) Notice: Subject to any disclaimer, the term of this patent is extended or adjusted under 35 U.S.C. 154(b) by 433 days.

This patent is subject to a terminal disclaimer.

(21) Appl. No.: 10/034,432

(22) Filed: Dec. 27, 2001

(65) Prior Publication Data

US 2003/0060718 A1 Mar. 27, 2003

Related U.S. Application Data

(63) Continuation-in-part of application No. 09/393,456, filed on Sep. 10, 1999, now Pat. No. 6,351,663.

(51) Int. Cl.[7] .................................................. A61B 6/00
(52) U.S. Cl. ........................ 600/431; 600/473; 424/9.6; 607/89
(58) Field of Search ................................ 600/473, 476, 600/431, 101, 108; 424/9.1, 9.6; 548/400, 416, 427; 252/70; 607/88, 89; 606/2, 4; 250/459.1

(56) References Cited

U.S. PATENT DOCUMENTS

| | | |
|---|---|---|
| 1,048,419 A | 12/1912 | Krumbiegel et al. |
| 2,895,955 A | 7/1959 | Heseltine et al. |
| 3,736,524 A | 5/1973 | Drexhage |
| 3,871,772 A | 3/1975 | Munnerlyn et al. |
| 3,893,447 A | 7/1975 | Hochheimer et al. |

(Continued)

FOREIGN PATENT DOCUMENTS

| | | |
|---|---|---|
| DE | 3124305 | 1/1983 |
| DE | 244492 | 4/1987 |
| DE | 3926652 | 4/1991 |
| EP | 0109846 | 5/1984 |
| EP | 0554643 | 8/1993 |

(Continued)

OTHER PUBLICATIONS

Maarek et al. "Fluorescence of indocyanine green in blood: intensity dependence on concentration and stabilization with sodium polyaspartate," Journal of Photochemistry and Photobiology B: Biology 65 (2001) 157–164.*

"Photosensitizer," Ophthamalmic Surgery and Lasers, vol. 28, No. 5, p 410 (1997).

(Continued)

Primary Examiner—Shawna J. Shaw
(74) Attorney, Agent, or Firm—Leydig, Voit & Mayer Ltd.

(57) ABSTRACT

Aqueous indocyanine green (ICG) composition exhibiting enhanced stability, as well as enhanced ICG concentration, as compared to presently available ICG products. The composition comprises an aqueous ICG composition comprising ICG at a concentration of at least about 10 mg/ml and an aqueous diluent, wherein the composition is stable for at least 24 hours. Diagnostic and therapeutic methods for using these aqueous compositions are also contemplated, e.g., angiography, dye-enhanced photocoagulation, photodynamic therapy, for a variety of conditions, including Age-Related Macular Degeneration (ARMD), lesions and tumors.

97 Claims, 5 Drawing Sheets

U.S. PATENT DOCUMENTS

| | | |
|---|---|---|
| 3,944,341 A | 3/1976 | Pomerantzeff |
| 4,056,310 A | 11/1977 | Shimizu et al. |
| 4,251,139 A | 2/1981 | Matsumura |
| 4,369,250 A | 1/1983 | Gindler |
| 4,412,543 A | 11/1983 | Vassiliadis et al. |
| 4,466,442 A | 8/1984 | Hilmann et al. |
| 4,541,438 A | 9/1985 | Parker et al. |
| 4,573,778 A | 3/1986 | Shapiro |
| 4,608,990 A | 9/1986 | Elings |
| 4,762,701 A | 8/1988 | Horan et al. |
| 4,786,813 A | 11/1988 | Svanberg et al. |
| 4,799,783 A | 1/1989 | Takahashi et al. |
| 4,821,117 A | 4/1989 | Sekiguchi |
| 4,835,103 A | 5/1989 | Cercek et al. |
| 4,842,401 A | 6/1989 | Maurice |
| 4,859,584 A | 8/1989 | Horan et al. |
| 4,978,213 A | 12/1990 | El Hage |
| 5,072,731 A | 12/1991 | Taratuta et al. |
| 5,092,331 A | 3/1992 | Nakamura et al. |
| 5,116,114 A | 5/1992 | Nakamura et al. |
| 5,126,235 A | 6/1992 | Hioki |
| 5,141,303 A | 8/1992 | Yamamoto et al. |
| 5,150,292 A | 9/1992 | Hoffmann et al. |
| 5,163,437 A | 11/1992 | Fujii et al. |
| 5,225,859 A | 7/1993 | Fleischman |
| 5,247,318 A | 9/1993 | Suzuki |
| 5,277,913 A | 1/1994 | Thompson et al. |
| 5,279,298 A | 1/1994 | Flower |
| 5,292,362 A | 3/1994 | Bass et al. |
| 5,303,709 A | 4/1994 | Dreher et al. |
| 5,315,998 A | 5/1994 | Tachibana et al. |
| 5,394,199 A | 2/1995 | Flower |
| 5,400,791 A | 3/1995 | Schlier et al. |
| 5,438,989 A | 8/1995 | Haglund et al. |
| 5,441,858 A | 8/1995 | Delprato et al. |
| 5,450,144 A | 9/1995 | Ben Nun |
| 5,552,452 A | 9/1996 | Khadem et al. |
| 5,569,587 A | 10/1996 | Waggoner et al. |
| 5,573,750 A | 11/1996 | Singh |
| 5,576,013 A | 11/1996 | Williams et al. |
| 5,618,733 A | 4/1997 | Sakata et al. |
| 5,624,597 A | 4/1997 | Buhl et al. |
| 5,643,356 A | 7/1997 | Nohr et al. |
| 5,648,062 A | 7/1997 | Klaveness et al. |
| 5,676,928 A | 10/1997 | Klaveness et al. |
| 5,691,204 A | 11/1997 | Kantor et al. |
| 5,707,608 A | 1/1998 | Liu |
| 5,707,986 A | 1/1998 | Miller et al. |
| 5,716,642 A | 2/1998 | Bagchi et al. |
| 5,719,027 A | 2/1998 | Miyazaki et al. |
| 5,747,475 A | 5/1998 | Nordquist et al. |
| 5,750,722 A | 5/1998 | Huynh et al. |
| 5,762,957 A | 6/1998 | Mehlhorn |
| 5,773,299 A | 6/1998 | Kim et al. |
| 5,798,349 A | 8/1998 | Levy et al. |
| 5,804,448 A | 9/1998 | Wang et al. |
| 6,248,727 B1 * | 6/2001 | Zeimer .................. 514/63 |
| 6,351,663 B1 * | 2/2002 | Flower et al. .......... 600/476 |
| 6,443,976 B1 * | 9/2002 | Flower et al. .......... 607/88 |
| 2002/0028474 A1 * | 3/2002 | Shibamura et al. ....... 435/7.23 |
| 2004/0156782 A1 * | 8/2004 | Alam et al. ............ 424/9.6 |

FOREIGN PATENT DOCUMENTS

| | | |
|---|---|---|
| EP | 0649667 | 4/1995 |
| EP | 0791361 A | 8/1997 |
| EP | 589825 | 5/1998 |
| GB | 2034916 | 6/1980 |
| JP | 87042892 | 9/1987 |
| WO | 95/24930 | 9/1995 |
| WO | 96/31237 | 12/1996 |
| WO | 97/31582 | 9/1997 |
| WO | 97/33620 | 9/1997 |
| WO | 97/46262 A | 12/1997 |
| WO | 00/41726 A | 7/2000 |

OTHER PUBLICATIONS

Desmettre et al., "Diode Laser–Induced Thermal Damage Evaluation on the Retina with a Liposome Dye System," *Lasers in Surgery and Medicine,* vol. 24, pp. 61–68 (1999).

Flower et al., "Evolution of Indocyanine Green Dye Choroidal Angiography," *Optical Engineering,* vol. 34, No. 3, pp. 727–736 (1995).

Flower et al., "Pulsatile Flow in the Choroidal Circulation: A Preliminary Investigation," *Eye,* vol. 4, pp. 310–318 (1990).

Flower et al., "Variability in Choriocapillaris Blood Flow Distribution," *Investigative Ophthalmology & Visual Science,* vol. 36, No. 7, pp. 1247–1258 (1995).

Flower, "Choroidal Angiography Today and Tomorrow," *Retina,* vol. 12, No. 3, pp. 189–190 (1992).

Flower, "Extraction of Choriocapillaris Hemodynamic Data from ICG Fluorescence Angiograms," *Investigative Ophthalmology & Visual Science,* vol. 34, No. 9, pp. 2720–2729 (1993).

Flower, "Injection Technique for Indocyanine Green and Sodium Fluorescein Dye Angiography of the Eye," *Investigative Ophthalmology,* vol. 12, No. 12, pp. 881–895 (1973).

Gathje et al., "Stability Studies on Indocyanine Green Dye," *Journal of Applied Physiology,* vol. 29, No. 2 pp. 181–185 (1970).

Holzer et al., "Photostability and Thermal Stability of Indocyanine Green," *J. Photochem. Photobiol. B: Biol.* vol. 47, pp. 155–164 (1998).

Klein et al., "An Image Processing Approach to Characterizing Choroidal Blood Flow," *Investigative Ophthalmology & Visual Science,* vol. 31, No. 4, pp. 629–637 (1990).

Miki et al., "Computer Assisted Image Analysis Using the Subtraction Method in Indocyanine Green Angiography," *European Journal of Ophthalmology,* vol. 6, No. 1, pp. 30–38 (1996).

DuBosar, "Population at Risk: Age–Related Macular Degeneration," *Ocular Surgery News,* 10 Pages, (May 15, 1998).

Chen et al., "Photothermal Effects on Murine Mammary Tumors Using Indocyanine Green and an 808–nm Diode Laser: an in vivo Efficacy Study,"*Cancer Lett.,* vol. 98, No. 2, pp. 169–173 (1996).

Alcon Pharmaceuticals Ltd. "Pharmacyclics Inc,"*The Business and Medicine Report,* p. 63 (Jan. 1998).

Shiraga et al., "Feeder Vessel Photocoagulation of Subfoveal Choroidal Neovascularization Secondary to Age–Related Macular Degeneration," *Ophthalmology,* vol. 105, No. 4, pp. 662–669 (1998).

Flower et al., "Clinical Infrared Absorption Angiography of the Choroid," *American Journal of Ophthalmology,* vol. 73, No. 3, pp. 458–459 (1972).

Flower et al., "A Clinical Technique and Apparatus for Simultaneous Angiography of the Separate Retinal and Choroidal Circulation," Investigative Ophthalmology, vol. 12(4), pp. 248–261 (1973).

Hochheimer et al., "Angiography of the Cervix," *John Hopkins Medical Journal,* vol. 135, pp. 375–382 (1974).

Flower, "High Speed Human Choroidal Angiography Using Indocyanine Green Dye and a Continuous Light Source," *International Symposium on Fluorescein Angiography, Documenta Ophthmologica* Proceedings Series, vol. 9, pp. 59–64 (1976).

Flower et al., "Indocyanine Green Dye Fluorescence and Infrared Absorption Choroidal Angiography Performed Simultaneously with Fluorescein Angiography," *Johns Hopkins Medical Journal,* vol. 138, No. 2 pp. 33–42 (1976).

Orth et al., "Potential Clinical Applications of Indocyanine Green Choroidal Angiography," *The Eye, Ear, Nose and Throat Monthly,* vol. 55, Jan., pp. 15–28, 58 (1976).

Patz et al., "Clinical Applications of Indocyanine Green Angiography," *International Symposium on Fluorescein Angiography, Documents Ophthmologica,* vol. 9 , pp.245–251 (1976).

Flower, "Choroidal Fluorescent Dye Filling Patterns a Comparison of High Speed Indocyanine Green and Fluorescein Angiograms," *International Ophthalmology,* vol. 2(3), pp. 143–150 (1980).

Hyvarinen et al., "Indocyanine Green Fluorescence Angiography," *ACTA Ophthalmologica,* vol. 58, pp. 528–538 (1980).

Bischoff et al., "Ten Years Experience with Choroidal Angiography Using Indocyanine Green Dye–A New Routine Examination or an Epilogue," *Doc Ophthalmology,* vol. 60(3), pp. 235–291 (1985).

Murphy et al., "Effects of Retinal Photocoagulation on the Choroidal Circulation," *Investigative Ophthalmology & Visual Science,* vol. 32(4), p. 785 (1991) Meeting Abstract.

Murphy et al., "Indocyanine Green Angiographic Studies of Occult Choroidal Neovascularization," *Investigative Ophthalmology & Visual Science,* vol. 34(4), p. 1134 (1993) Meeting Abstract.

Flower, "Binding and Extravasation of Indocyanine Green Dye,"*Retina,* vol. 14, No. 13, pp. 283–284 (1994).

Lim et al., "Indocyanine Green Angiography," *International Ophthalmology Clinics,* vol. 35(4), pp. 59–70 (1995).

Hiner et al., "A Previously Undescribed Indocyanine Green Angiographic Filling Pattern," *Investigative Ophthalmology & Visual Science,* vol. 36, No. 4 (1995) Summary Meeting Abstract.

Flower et al., "Disparity Between Fundus Camera and Scanning Laser Ophthalmoscope Indocyanine Green Imaging of Retinal Pigment Epithelium Detachments,"*Retina,* vol. 18(3), pp. 260–268 (1998).

Staurenghi et al., "Laser Treatment of Feeder Vessels in Subfoveal Choroidal Neovascular Membranes," *Ophthalmology,* vol. 105, No. 12, pp. 2297–2305 (1998).

Flower et al., "Expanded Hypothesis on the Mechanism of Photodynamic Therapy Action on Choroidal Neovascularization," *Retina,* vol. 19, No. 5 pp. 365–369 (1999).

Flower, "Experimental Studies of Indocyanine Green Dye–Enhanced Photocoagulation of Choroidal Neovascularization Feeder Vessels," *American Journal of Ophthalmology* vol. 129, No. 4, pp. 501–512 (2000).

Mendelson et al., "Amelioration of Experimental Lipid Keratopathy by Photochemically Induced Thrombosis of Feeder Vessels,"*Arch Ophthalmol,* vol. 105, Jul.1987 (pp. 983–988).

Tsilimbaris et al., "Photothrombosis Using Two Different Phthalocyanine Administration Routes: Continuous I.V. Infusion v. Bolus I.V. Injection," *Photochem. Photobiol.,* 62(3), 1995, (pp. 435–441).

Spinelli et al., "Endoscopic Treatment of Gastrolintestinal Tumors: Indications and Results of Laser Photocoagulation and Photodynamic Therapy," *Seminars in Surgical Oncology,* 11 (4), 1995, (pp. 307–318) (Abstract only).

Von Kerczek et al., "The Effects of Indocyanine Green Dye–Enhanced Photocoagulation on the Blood Flow in the Choriocapillaris and the Choroidal Neovascularization," *Advances in Heat and Mass Transfer in Biotechnology,* 2000, (pp. 1–3). (Abstract only).

IC–Green ™ (Sterile Indocyanine Green); Product insert; Akorn, Inc. (2001).

* cited by examiner

Fig. 3 Stability of IC-Green (5 mg/mL) Reconstituted with WFI and Specialized Diluent

INDOCYANINE GREEN (ICG) COMPOSITIONS AND RELATED METHODS OF USE

RELATED APPLICATIONS

This application is a continuation-in-part of co-pending U.S. patent application Ser. No. 09/393,456, filed Sep. 10, 1999, now U.S. Pat. No. 6,351,663 which is incorporated by reference.

FIELD OF THE INVENTION

The present invention generally concerns indocyanine green compositions useful in the diagnosis of organ function and disease in animals, e.g., humans.

BACKGROUND OF THE INVENTION

Indocyanine green (ICG) is a well-known fluorsecent dye. The dye is presently marketed by Akorn, Inc. (Buffalo Grove, Ill.) under the trademark IC GREEN™. ICG is presently supplied as a lyophilized powder (25 mg) for reconstitution with 5 ml sterile water for injection (WFI), or for reconstitution at 20 mg/ml in WFI. The reconstituted ICG composition (at 5 mg/ml) should be used within 10 hours, with any unused portion being discarded.

The U.S. Food and Drug Administration has approved this dye as an injectable drug for use in determining hepatic function, cadiac output and liver blood flow, as well as for opthalmic angiography. In opthalimic angiography, the ICG is excited to fluorescence by radiation, permitting angiograms of the opthalmic vasculature to be obtained.

Although currently available aqueous ICG compositions provide adequate levels of ICG for use in the approved indications, the solubility of ICG in WFI decreases as the concentration exceeds 5 mg/ml. Thus, a need exists for an aqueous ICG composition that exhibits beneficial properties exceeding those possessed by the currently approved compositions, particularly with respect to enhancements in ICG concentration and stability.

SUMMARY OF THE INVENTION

In one aspect, the present invention provides an ICG composition that exhibits enhanced stability, as well as enhanced ICG concentration, as compared to presently available ICG products. The composition comprises an aqueous ICG composition comprising ICG at a concentration of at least about 10 mg/ml and an aqueous diluent, wherein the composition is stable for at least 24 hours. In a related aspect, the invention provides a stable ICG liposomal formulation.

Among others, the inventive compositions provide enhanced angiographic resolution relative to that provided by the currently approved ICG composition, as well as certain economic advantages. For example, the same ICG composition may be administered to a given patient over a course of several days, as opposed to preparing a fresh composition prior to each administration.

Other aspects of the present invention include methods for using the inventive compositions. These methods include the presently approved uses, and the diagnosis and treatment of age-related macular degeneration (ARMD)-related choroidal neovascularization (CNV), tumors, and other undesirable lesions fed by newly-formed and existing blood vessels. Illustrative techniques useful in these methods include angiography, dye-enhanced photocoagulation of blood vessels, photodynamic therapy (PDT), and combinations thereof.

When administered in connection with angiography, the relatively high concentration ICG formulations of the present invention permit more rapid and accurate identification of vessels, e.g., vessels that feed blood to a lesion. When treatment of the feeder vessel or lesion, such as a tumor or CNV, via dye-enhanced photocoagulation is desired, the inventive compositions provide faster and more permanent occulsion of these abnormalities. Further, less energy is required to occlude the abnormalities as opposed to the energy required using conventional ICG compositions.

The inventive ICG compositions have been administered to rats and found to be safe when measured by hematology, clinical chemistry, histology and pathology of tissue samples.

These and other features and advantages of the present invention will become apparent upon review of the following figures and detailed description of the preferred embodiments of the present invention.

DETAILED DESCRIPTION OF THE INVENTION

Figure 1:
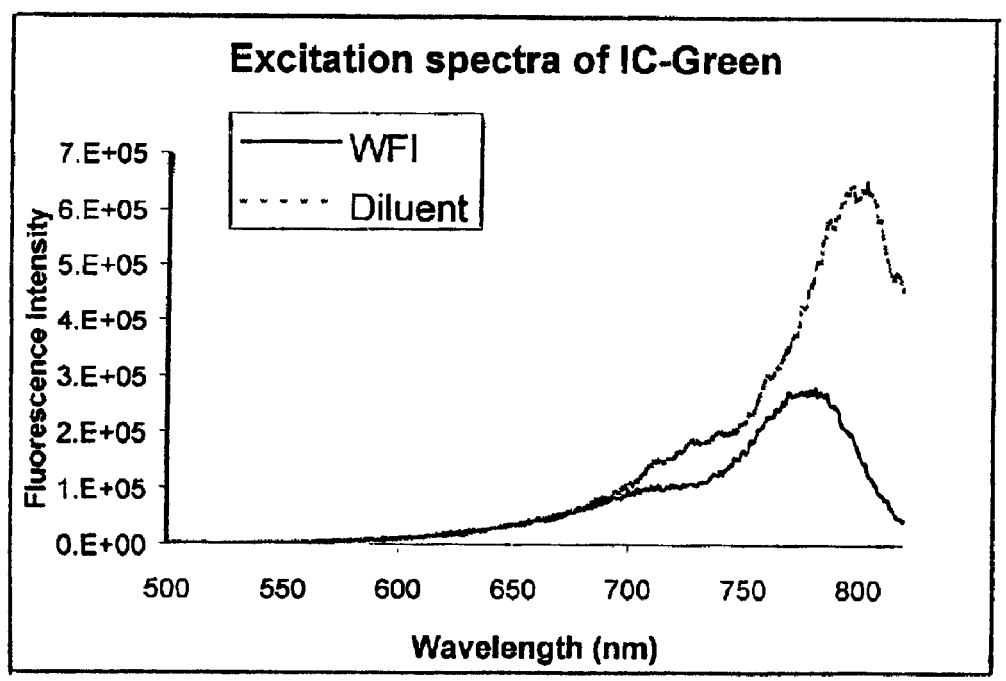
FIG. 1 is a graph demonstrating the excitation fluorescence spectra between 500 and 820 nm of a preferred ICG formulation of the present invention using Water For Injection (WFI) as the water source.

In one aspect, the present invention provides aqueous ICG compositions that provide for a relatively higher ICG concentration and greater stability relative to the currently approved product. In a preferred aspect, the inventive formulations provide at least 10 times, more preferably at least 15 times, the present ICG concentration, while also possessing a stability of at least 10, and more preferably at least 15, times relative to the currently-approved ICG product.

The inventive compositions comprise ICG at a concentration of at least 10 mg/ml and an aqueous diluent, wherien the ICG is stable for at least 24 hours. Advantageously, the ICG is stable in the aqueous compostion for at least 48 hours, preferably for at least 3 days, more preferably for at least 5 days, and most preferably for at least 7 days, despite the ICG being present at relatively high concentrations.

The amount of ICG that may benefit from the stability provided by the inventive diluent varies widely, from about 1 mg/mL up to about 100 mg/mL. Of course, benefits of the present invention will be obtained at ICG concentrations exceeding that which is presently approved. Advantageously, then, enhanced solubility and/or stability is desired, and should be noticed, at ICG concentrations of at least about 10 mg/ml, 20 mg/ml, 25 mg/mL, 50 mg/mL, 75 mg/mL, and up to at least about 100 mg/mL, and at ranges therebetween.

The ICG used in the inventive composition may be provided in any suitable form, but is most commonly provided in a sterile lyophilizate. When provided as a lyophilizate, the ICG is reconstituted prior to adminstration by use of the aqueous diluent described herein. To effect the reconstitution, water, in the form of sterile WFI, may be introduced into a vial holding the ICG, with the aqueous diluent being added thereafter. Alternatively, the WFI and aqueous diluent may be added in reverse order. Preferably, however, the aqueous diluent is in a vial separate from the ICG vial, with the aqueous diluent being introduced into the ICG-containing vial in an amount sufficient to provide the desired final ICG concentration, more preferably without the need for additional dilution to obtain the desired final ICG concentration.

The ICG and diluent may also be packaged together, e.g., as a kit, or in a dual chamber configuration, such as a pre-loaded dual chamber syringe or vial. Such syringes and vials maintain separation between the ICG and diluent, but permit mixing upon activation, prior to administration.

The aqueous diluent advantageously comprises a solubilizer and alcohol, with water (preferably sterile WFI) being added to reach the desired dilution. Desirably, the solubilizer is provided, per ml of diluent, at about 0.5 to about 5 mg, with the alcohol provided at about 50 to about 150 mg on the same basis.

While not wishing to be bound to any particular theory, the solubilizer is theorized to assist in solubilizing the ICG in the aqueous diluent, while also enhancing the stability of the final ICG composition. Suitable solubilizers for use in the inventive composition include surface active agents (also referred to as surfactants) and cosolvents (e.g., polyethylene glycol). Surfactants are preferred, with liquid (at 25° C.) nonionic surfactants being most preferred, e.g., Tweens, such as polysorbate 80. In either case, the solubilizer is advantageously a liquid (no more than about 5 cp viscosity, preferably no more than about 3 cp, and most preferably about 1 cp, at 25° C.), e.g., polyethylene glycol having a molecular weight of less than about 800, and more preferably less than about 500. This will assist in promoting solvation of the ICG in the diluent, and enhance the ability of the aqueous ICG composition to be injected into the bloodstream.

The solubilizer should be present in the ICG composition in an amount sufficient to enhance the solubility of the ICG in the composition relative to the same composition without the solubilizer, and also relative to the solubility of the presently approved ICG compositions. However, is was unexpectedly found that the inclusion of excessive levels of solubilizer in these relatively concentrated compositions adversely affected the composition stability. Desirably, then, the amount of solubilizer is limited to that which provides the aqueous composition with a stablizing effect, typically no more than about 7 mg/ml of the aqueous diluent, and advantageously no more than about 5 mg/ml. More preferably, the solubilizer is present at from about 0.1 mg/ml, and is more preferably present at from about 0.25 mg/ml to about 5 mg/ml of the aqueous diluent.

Generally, the ratio of solubilizer to ICG in the aqueous ICG composition, on an absolute weight basis, may range from about 0.1:100 to about 7:10, advantageously from about 0.2:100 to about 5:75, and preferably from about 0.2:75 to about 3:75.

A lower alkyl alcohol is also included in the composition, in part due to its ability to enhance the solubility of ICG in the diluent, as well as enhance the fluorescence of ICG. While a variety of pharmaceutically-acceptable alcohols may be used, lower alkanols ($C_{2-6}$ alcohols), diols and triols are advantageously utilized, e.g., ethyl alcohol, glycerine, propylene glycol and mixtures thereof. Ethyl alcohol is preferred, due to its low cost, pharmaceutical-acceptability and wide availability.

Generally, sufficient alcohol should be included in the diluent to provide enhanced solubility and/or fluorescence of ICG relative to the same composition without alcohol, and also relative to the presently approved ICG composition. Generally, the ratio of alcohol to ICG on a weight basis may range from about 1:0.25 to about 1:4, is preferably about 1:0.5 to about 1:3, and most preferably about 1:1 to about 1:2.5. Optimally, the ratio is about 1:2. On a weight percentage basis, the alcohol should be present in the aqueous diluent from about 25 mg/ml to about 250 mg/ml of the diluent, advantageously from about 50 mg/ml to about 200 mg/ml, and preferably from about 75 to about 125, to about 150 mg/ml.

The amount of alcohol in the diluent is further preferably greater than the amount of solubilizer. The former is preferably present in at least 50 wt. % excess, up to and including about 200 wt. % excess, relative to the solubilizer. More preferably, the alcohol is at least 75 wt. %, up to and including 150 wt. %, and most preferably about 85 wt. % to about 125 wt. %, relative to the weight of solubilzer.

The diluent further desirably includes polyvinyl pyrrolidone (PVP). This component is believed to contribute to the stability of the composition, and is therefore included in a stability-enhancing amount. Generally, this component may be present in the aqueous composition, per ml of diluent, from about 10 to about 100 mg, advantageously from about 25 to about 75 mg, and preferably from about 40 to about 60 mg. As PVP is a polymer, and available at a variety of molecular weights, it is desirable to utilize a relatively low molecular weight PVP (less than about 30,000, preferably less than about 15,000) to assist in maintaining the viscosity of the aqueous composition at a relatively low level.

Preferably, but optionally, the diluent includes an antimcrobial agent. This component assists in maintaining the sterility of the diluent during storage. While any number of pharmaceutically-acceptable antimicrobials may be used, an antimicrobial that does not adversely affect the solubility and other beneficial properties of the aqueous ICG composition is preferred. Illustrative of such antimicrobials are those containing alcohol functionalities, such as benzoyl alcohol.

The amount of antimicrobial agent is advantageously that which provides the foregoing advantages, including imparting antimicrobial activity to the diluent during storage and the aqueous ICG composition. Preferably, the antimicrobial is provided, per ml of diluent, at from about 5 mg to about 10 mg per ml of diluent.

The water included in the inventive composition is preferably sterilized, e.g., WFI. The amount of water used in the diluent is that required to provide the desired level of ICG concentration in the ICG compositions, as well as the desired weight percentages of the other diluent components.

As an alternative, one or more of the diluent components may be lyophilized with the ICG. For example, and if included, a pH adjusting agent and/or antimicrobial agent may be lyophilized with the ICG and retained within the ICG vial until reconstitution with the remaining components of the diluent. Other such combinations of diluent components and ICG are possible, depending on the ability of each particular diluent component to sucessfully undergo lyophilization with the ICG.

A related aspect of the present invention is a liposomal ICG formulation. In this formulation, the ICG is provided as a lyophilizate which, upon reconsitution with a diluent comprising water (e.g., WFI, saline, and liposome-forming components), provides for enacapsulation of the ICG in liposomes. Alternatively, the liposome-forming components may be included with the ICG in the lyophilizate composition. After reconstitution, the ICG is desirably present at a concentration of about 0.5 to about 3 mg/ml of the formulation, and more desirably from about 1 to about 2 mg/ml. When reconstituted, the liposomal formulation may comprise from about 1 to about 100 mg ICG.

The liposome-forming components may be selected from those which are pharmaceutically-acceptable. Illustrative components include dl-alpha tocopheryl acetate (about 0.1 to about 1 mg), cholesterol (about 5 to about 50 mg), egg phosphatidylcholine (about 10 to about 100 mg) and tertiary butyl alcohol (about 0.1 to about 10 ml), on a per ml basis.

The inventive composition provides the further advantage of relatively low viscosity, rendering it suitable for parenteral administration. More specifically, the viscosity of the diluent, after one month of storage at ambient (25° C.) temperature, will advantageosly remain less than about 5 centipoise, and preferably less than about 3 cp. The aqueous ICG composition desirably remains less than about 5 cp, preferably less than about 3 cp, and most preferably about 1 cp, up to one week after reconstitution.

A pH adjustment of the reconstituted compositon to between about 6 to about 8 may optionally be completed using effective amounts of any of a number of pharmaceutically-acceptable acids, bases and/or buffer systems. Preferably, an acid and/or base is used in an effective amount, e.g., HCl, NaOH, to adjust the pH of the reconstituted composition to its preferred level of about between about 6.5 and 7.5, and more preferably about 7.

Related aspects of the present invention concern methods of using the compositions herein described. These methods are claimed and described as a series of diagnostic and/or treatment steps. It should be understood that these methods and associated steps may be performed in any logical order. Moreover, the methods may be performed alone, or in conjunction with other diagnostic procedures and treatments administered before, during or after such methods and steps set forth herein without departing from the scope and spirit of the present invention. It is further contemplated that the term animals, as used herein, includes, but is not limited to, humans.

As used herein, stability may be described in terms of a drop in potency of the ICG compositions. For example, the drop in potentcy is desirably less than about 10%, preferably less than about 7%, more preferably less than about 5%, and most preferably less than about 2%, after one or more of the aforementioned time periods (e.g., 24 hours, 48 hours, 3 days, one week, 2 weeks, 3 weeks and 4 weeks, etc.), when stored in a 25° C. environment, and under refrigerated conditions (i.e., between 4–8° C.). Preferably, the aqueous ICG composition will also possess one or more of the following attributes: no visual precipitate (naked eye, preferably under 25×, and more preferably under 50× examination), no color change (as viewed by the naked eye relative to a freshly prepared equivalent ICG composition), no loss in sterility, and/or no greater than about 2 wt. %, and more preferably no greater than about 1 wt. % degradation product, over one or more of the aforementioned time periods. A determination of relative composition potency may be obtained using HPLC. Sterility may be measured using any one of several tests therefor sanctioned by the U.S. Food and Drug Administration.

The aforementioned stability parameters may also be used in the evaluation of the inventive aqueous ICG compositions under accelerated testing. For example, when the compositions are placed in a 40° C. environment, they desirably remain stable for at least 4 hours, preferably for at least 8 hours, and more preferably for at least 12 hours.

The ICG and diluent may be packaged in any suitable manner, e.g., vials made of glass, plastic or other pharmaceutically-acceptable materials. The diluent and aqueous ICG compositions are desirably protected from exposure to light in a green, amber or opaque container. Preferably, the ICG and diluent are packaged in a multi-chambered vessel which segregates the ICG from the diluent until the aqueous ICG composition is required for therapy. Examples of suitable multi-chambered vessels include a dual-chamber by-pass syringe and a dual chambered vial which enables mixing of the ICG ad diluent as desired.

A further aspect of the present invention contemplates methods for using the foregoing ICG compositions. These methods are generally diagnostic and/or therapeutic in nature. In one preferred aspect, the invention provides for the same diagnostic methods as those currently approved for ICG, but use the inventive ICG compositions described herein as the ICG source instead of the standard aqueous ICG formulation. For example, the inventive compositions may be used in obtaining angiographic images in association with the diagnosis of any disease or condition in which angiography is a useful diagnostic tool. Such diagnostic procedures are well known, and continue to be developed, e.g., the diagnosis of CNV.

Other method contemplated by the present invention concern the diagnosis and/or treatment of conditions, particularly lesions, the treatment aspect using the inventive composition in dye-enhanced photocoagulation. Generally, in this method, radiation of a certain wavelength (based upon the dye used) is applied onto an undesired portion of a dye-carrying blood vessel, e.g., a vessel that carries, or feeds, blood to the lesion. The radiation, once a wavelength is applied that will "excite" the dye, causes the temperature of the dye to increase upon absorption of the radiation. While not desiring to be bound to any particular theory, as the dye temperature increases, the temperature of the surrounding blood and vessel tissue also increases. This increase in temperature hastens the rate at which blood clots in and adjacent that portion of the vessel onto which the radiation is applied. This clotting, in turn, leads to partial, or preferably complete, obstruction of the vessel in or adjacent the portion of the vessel onto which the radiation was applied. This obstruction will, in many instances, provide for subsequent reduction in the lesion. Alternatively, or in connection with this therapy, the lesion itself may be irradiated in the presence of the dye.

It is well known that the peak absorption and emission of ICG lies in the range of 800–850 nm. Thus, a light source emitting such wavelength should be used when obtaining angiographic images during a diagnostic procedure, as well as during any therapeutic procedure (with power being modulated accordingly).

It should be appreciated that in connection with the inventive methods (e.g., diagnosis of lesions such as CNV, tumors and abnormal vasculature), the amount of ICG administered should be sufficient to permit the dye to fluoresce when radiation at the appropriate wavelength is applied, thereby providing useful angiographic images. The same standard is applicable to the therapeutic methods; sufficient dye should be utilized to enable the desired treatment. This information may be readily determined by those skilled in the art, and should be at least that concentration currently accepted for use in ophthalmic angiography, e.g., for diagnosis, 2 ml of a 20 mg/mL ICG solution (IC-GREEN™). Of course, the relatively higher dye concentrations described herein may advantageously be used in any of these diagnostic and treatment methods.

Any suitable source of radiation that causes the particular dye to fluoresce as it flows through the vessels of interest may be used in the present methods. The type and amount of energy applied to the blood vessels of interest must be sufficient to cause the fluorescent dye present in these blood vessels to fluoresce. The energy applied must be within the limits of the maximum flux density or irradiance which can be applied to the blood vessels of interest within a particular time span without causing excessive damage to the normal surrounding tissue. The longer the duration of exposure to the energy source, the lower the allowable level of irradiance. The particular energy source and amount of energy applied will depend upon the type of fluorescent dye administered to the subject.

The radiation used in the methods described herein is preferably applied using a laser, and, most preferably, using a pulsed laser. The pulsing of the laser provides the advantage of generating a greater number of photons for image formation in the shortest time interval. Various devices, preferably fundus cameras for ophthalmic diagnoses and therapies, can be adapted for providing an appropriate level and type of radiation in accordance with the teachings provided herein. The latter include, for example, those described in U.S. Pat. Nos. 5,279,298, 5,394,199 and 5,400,791. Preferably, a fundus camera having two sources of radiation (e.g., lasers) is provided. Using such a camera, one laser can be used to irradiate the general area of interest so any ocular vessels requiring treatment can be identified, while the second laser can be used almost immediately upon identification of the vessel to be treated to hasten the coagulation of the blood therein, i.e., dye-enhanced photocoagulation. The ability to aim the treatment laser using the identical view used to obtain the angiograms is a significant advantage. Further, the ability to complete the diagnosis and treatment steps within minutes, e.g., advantageously in less than about 30 and preferably less than about 15 minutes, lessens patient trauma and increases overall treatment efficiency.

The inventive methods further contemplate the administration of the inventive composition in order to permit visualization of vessels at locations other than in the eye. Generally, angiograms of blood vessels and other abnormalities associated with blood vessels may be obtained at any location in an animal in which readable angiographic images can be obtained. For example, hollow organs and body cavities may be subjected to the inventive methods, e.g., the interior wall of the bladder, stomach, lung, gastrointestinal tract, bladder, pancreas, gall bladder, sinus, liver, kidney, heart, cervix, ovary, prostate, stomach, trachea, skin or colon may be explored, as well as the exterior walls of those organs, and the brain. This permits the diagnosis (including, e.g., the monitoring of prior treatments or of prior-diagnosed conditions) and treatment of lesions, e.g., abnormal blood vessels, such as aneurysms, ruptured blood vessels, as well as the diagnosis and treatment of tumors associated with those and other body cavity tissues.

An endoscope may advantageously be used to obtain the previously mentioned angiograms. The endoscope would be inserted into the body and positioned adjacent the area of interest. A first instrument would be used with the endoscope to provide radiation at an appropriate wavelength, e.g., a laser optic cable, to cause the ICG dye within the subject vessels to fluoresce so an angiogram can be obtained. Similarly, a second instrument would be used with the endoscope that would permit an angiographic image of the fluorescing ICG dye within the vessels to be obtained. For example, an optical device connected to a CCD camera, such as those used to perform a colonoscopy and other invasive procedures that permit a physician to view the interior of a body cavity, presently exists, and such technology may be readily adapted for use in conjunction with the endoscopic procedures of the present invention.

After injection of the dye composition, and flow of the composition through the region expected to be afflicted, an angiogram would then be obtained using what are referred to herein as the first and second instruments, and any abnormal vessels detected thereby treated, using the procedures described previously for diagnosis and treatment.

In the context of the present invention, the term "body cavity" includes any cavity that permits the introduction of an endoscope or other instrument that permits the use of appropriate radiation and imaging equipment required to obtain an angiogram. Illustrative of body tissues associated with suitable cavities are the eye, lung, gastrointestinal tract, bladder, pancreas, gall bladder, sinus, heart, cervix, brain, trachea, ovaries, prostate, stomach and skin.

Treatment is preferably effected by applying radiation upstream of the lesion, e.g., upstream of the ruptured blood vessel, the vessel feeding the tumor, or adjacent and upstream of the abnormal blood vessels, after administration of the dye composition. The radiation is desirably applied as the dye bolus first enters the vessel to be treated, whereby the flow of blood through the vessel is reduced. Permitting the ICG to circulate within the body for permits the ICG to stain the walls of those tissues that are contacted by the ICG. This may result in undesired portions of the tissue being treated. While not desiring to be bound to any particular theory, when radiation is applied, the temperature of any liquid adjacent the ICG dye receiving the radiation is raised, and the blood clotting is hastened, thereby reducing, e.g., partially or completely preventing, the flow of blood through the vessel. Varicose veins may also be treated using the aforementioned treatment methods.

When the treatment of a tumor, advantageously a solid tumor, is undertaken, the method of the present invention is preferably used in combination with other treatment agents. For example, therapeutically-effective amounts of chemotherapeutic agents, such as cisplatin, carboplatin, doxorubicin, paclitaxel, taxotere, methotrexate, fluorouracil, camptothecin, cyclophosphamide and mixtures thereof, may be administered, as well as therapeutically-effective amounts of anti-angiogenesis agents, either alone or in combination, may be administered. The identity of suitable anti-tumor and anti-angiogenesis agents and associated dosage regimens are well known, and as such will not be repeated herein. The timing of administration of these agents may occur at any time so long as the administration does not interfere with the treatment method of the present invention. Advantageously, however, the agents may be administered in combination with the dye-enhanced photocoagulation treatment methods described herein. For example, the agents can be administered immediately after dye-enhanced photocoagulation of tumor feeder vessels, and preferably are injected directly into the tumor. This provides several advantages including the reduction of trauma to the patient because multiple treatment agents are administered in a single procedure, the chemotherapeutic and anti-angiogenesis agents are delivered directly to the tumor thereby limiting the exposure of healthy tissue to these toxic agents (as would be the case using conventional IV administration), and conventional radiation can be narrowly focused on the tumor itself, as opposed to conventional methods that irradiate an area surrounding the tumor.

Conventional radiation treatment, mentioned previously, surgical intervention, and photodynamic therapy (PDT, the latter using the inventive ICG compositions, under conditions which produce, as presently theorized, the production of singlet oxygen which damages the targeted tissue) may also be used individually or in combination, before, after and in some cases, if feasible, during, the diagnostic and/or treatment methods of the present invention have been used. Preferably, PDT is applied after the dye-enhanced photocoagulation therapy described herein, and more preferably without further administration of ICG. If a need for additional ICG is indicated, however, the original and additional ICG is advantageously obtained from the same source (e.g., vial).

When diagnosis of the tumor is made in accordance with the angiogram methodology of the present invention, the location and boundaries of the tumor may be determined with a high degree of precision, without resort to the use of more harmful diagnostic procedures, e.g., X-rays. The precision provided by the present invention permits the treatment agents described previously to be more efficient because they are applied with a high degree of precision onto just the tumor itself, as compared to conventional methods, e.g., systemic administration of chemotherapeutic agents and application of radiation, which are applied over a more general area. This precise focus, in turn, lessens trauma to the subject by minimizing the side effects of these toxic agents.

The following examples are illustrative of preferred embodiments of the invention, and should not be considered as limiting the invention as defined by the appended claims in any respect.

COMPARATIVE EXAMPLE A

Baseline data concerning a commercial ICG formulation was obtained as follows:

| Formulation | Per ml | Total |
| --- | --- | --- |
| Indocyanine Green | 5 mg | 5 g |
| WFI | 1 ml | 1000 ml |

5 g ICG was added to 1000 ml of WFI and mixed in a suitable container until the ICG was completely dissolved. The resulting solution was sterilized by filtration through a 0.2 micron filter. 5 ml of the sterile solution was introduced into sterile vials and lyophilized. The vials were then stoppered, each including 25 mg ICG. The lyophilized formulation was found to be stable for a minimum of 2 years.

The sterile, lyophilized 25 mg of ICG in a vial prepared by the procedure described above was reconstituted with 5 ml of sterile WFI to provide a 5 mg/ml solution. The reconstituted solution was stable for about 10 hours when stored in a 25° C. environment (e.g., no visible precipitates, decline in potency was less than about 10%, no color change, and degradation products were less than 2 wt. %).

The maximum concentration of ICG in WFI was found to be about 25 mg/ml. When formulated at an ICG concentration of 50 mg/ml to 75 mg/ml using WFI as the lone diluent, the resulting composition had a paste-like consistency.

EXAMPLE 1

This is an example of a preferred formulation of the present invention, which provides both relatively high ICG concentration and stability compared to the commercially available ICG formulation, with a neutral pH.

| Formulation | Per ml | Total |
| --- | --- | --- |
| Indocyanine Green | 10 mg | 10 g |
| WFI | 1 ml | 1000 ml |

10 g of ICG was added to 1000 ml WFI and mixed in a suitable container until the ICG was completely dissolved. The solution was then sterilized through filtration using a 0.2 micron filter. 5 ml of the sterile solution was introduced into a series of sterile vials and lyophilized. The vials were then stoppered, each including 50 mg ICG. The lyophilized formulation was found to be stable for at least 2 years.

A diluent for reconstitution of the lyophilized ICG was prepared as follows:

| Formulation | Per ml | Total |
| --- | --- | --- |
| Polyvinyl pyrrolidone | 50 mg | 50 g |
| Ethanol | 100 mg | 100 g |
| Polysorbate 80 | 2 mg | 2 g |
| Benzyl Alcohol | 10 mg | 10 g |
| Sodium Hydroxide, qs pH | 7.0 | 7.0 |
| Water for Injection, qs ad | 1 ml | 1000 ml |

The diluent was prepared by mixing 100 g ethanol with 10 g benzyl alcohol in a suitable container. 2 g polysorbate 80 was then added, also via mixing. 50 g polyvinyl pyrrolidone was then added and dissolved therein. Sufficient sodium hydroxide solution was added to adjust the pH to 7.0. WFI was added to bring the solution to 1000 ml. The solution was then filtered through a 0.2 micron filter, and 5 ml of the solution was introduced into a series of sterile vials. The formulation was found to be stable for at least 7 days when stored in a 25° C. environment.

Sterile lyophilized 50 mg ICG was reconstituted with the aforedescribed diluent to provide a 50 mg/ml ICG solution. The reconstituted solution was found to be stable for at least 7 days when stored in a 25° C. environment, demonstrating superiority over the present commercial ICG formulation described in Comparative Example A. Specifically, with respect to an ICG concentration of 5 mg/ml, the 50 mg/ml inventive formulation was about 10 times more concentrated. Surprisingly, and despite the increase in concentration, the stability of the latter was about 17 times that of the former.

EXAMPLE 2

This is a further example of a preferred formulation of the present invention, which provides a relatively higher ICG concentration and similar stability relative to the ICG formulation described in Example 1.

| Formulation | Per ml | Total |
| --- | --- | --- |
| Indocyanine Green | 15 mg | 15 g |
| Water for Injection, qs ad | 1 ml | 1000 ml |

15 g of ICG was added to 1000 ml WFI and mixed in a suitable container until the ICG was completely dissolved. The solution was then sterilized through filtration using a 0.2 micron filter. 5 ml of the sterile solution was introduced into a series of sterile vials and lyophilized. The vials were then stoppered, each including 75 mg ICG. The lyophilized formulation was found to be stable for at least 2 years.

A sterile lyophilized 75 mg ICG vial was reconstituted with a vial of the diluent described in Example 1 to provide a 75 mg/ml ICG solution. The reconstituted solution was found to be stable for at least 7 days when stored in a 25° C. environment, demonstrating superiority over the present commercial ICG formulation described in Comparative Example A. Specifically, with respect to an ICG concentration of 5 mg/ml, the 75 mg/ml inventive formulation was about 15 times more concentrated. Surprisingly, and despite the increase in concentration, the stability of the latter was about 17 times that of the former.

EXAMPLE 3

This is a further example of a preferred formulation of the present invention. This formulation is the same as that described in Example 2, except that sodium hydroxide is included with the ICG in the lyophilized vial. This change does not adversely affect the ability to provide a highly concentrated ICG solution upon reconstitution, nor the stability of that solution.

| Formulation | Per ml | Total |
| --- | --- | --- |
| ICG | 15 mg | 15 g |
| Sodium Hydroxide, qs pH | 7.0 | 7.0 |
| WFI | 1 ml | 1000 ml |

15 g indocyanine green is added to 800 ml water for injection and dissolved in a container. Sufficient sodium hydroxide solution is added to adjust pH to 7.0. Remaining water for injection is added to bring the solution to 1000 ml. The solution is sterilized by filtration through 0.2 micron filter. 5 ml of the sterile solution is filled into sterile vials and lyophilized. The vials are then stoppered to provide 75 mg indocyanine green per vial. The formulation is stable for a minimum of 2 years.

Sterile lyophilized 75 mg ICG vial was reconstituted with the diluent described in Example 1 to provide a 75 mg/ml ICG solution. The reconstituted solution was found to be stable for at least 7 days when stored in a 25° C. environment, demonstrating superiority over the present commercial ICG formulation described in Comparative Example A. Specifically, with respect to an ICG concentration of 5 mg/ml, the 75 mg/ml inventive formulation was about 15 times more concentrated. Surprisingly, and despite the increase in concentration, the stability of the latter was about 17 times that of the former.

EXAMPLE 4

This is an example of another preferred embodiment of the present invention, a stable liposomal ICG formulation.

| Formulation | Per ml | Total |
| --- | --- | --- |
| ICG | 2.5 mg | 2.5 g |
| dl-alpha tocopheryl acetate | 0.37 mg | 0.37 g |
| Cholesterol | 7.0 mg | 7.0 g |
| Egg Phosphatidylcholine | 23.0 mg | 23.0 g |
| t-butyl alcohol, qs ad | 1.0 ml | 1000 ml |

In preparing this formulation, 0.37 g dl-alpha tocopheryl acetate as dissolved in 900 ml t-butyl alcohol. 2.5 mg ICG was added thereto, and dissolved while mixing. With mixing continuing, egg phosphatidylcholine was added, followed by the addition of cholesterol. Mixing continued, with sufficient t-butyl alcohol added to bring the solution to 1000 ml. The solution was passed through a 0.2 micron filter, with 10 ml of the now sterile (filtered) solution being filled aseptically in a sterile vial. The vials were partially stoppered with a sterile stopper, and lyophilized to provide a dried cake. The lyophilizing chamber is then flushed with nitrogen to maintain an inert atmosphere, with the vials then being stoppered while in that atmosphere to maintain sterility. This liposomal (lyophilized) formulation is stable for two years. The contents of the lyophilized composition in the vial may be reconstituted with WFI or normal saline. When so reconstituted, the liposomes may be formed by gentle agitation or sonication, and remains stable for at least 24 hours.

Formulation Stability

The stability of formulations in the foregoing examples was determined by high pressure liquid chromatography (HPLC), as described below.

The equipment used to perform the analysis was a Hewlett Packard HPLC system equipped with 1050 series pumps, a 100 series variable wavelength detector and a 1050 series autosampler. The column was Supelcosil LC-18-DB, 150×4.66 mm, 3 um, with the analysis performed using the following gradient solution:

| Time (Min) | % Solvent A | % Solvent B |
| --- | --- | --- |
| 0 | 90 | 10 |
| 20 | 20 | 80 |
| 25 | 20 | 80 |
| 30 | 90 | 10 |
| 35 | 90 | 10 |

Solvent A: 0.1% v/v Phosphoric Acid
Solvent B: Acetonitrile

Figure 3:
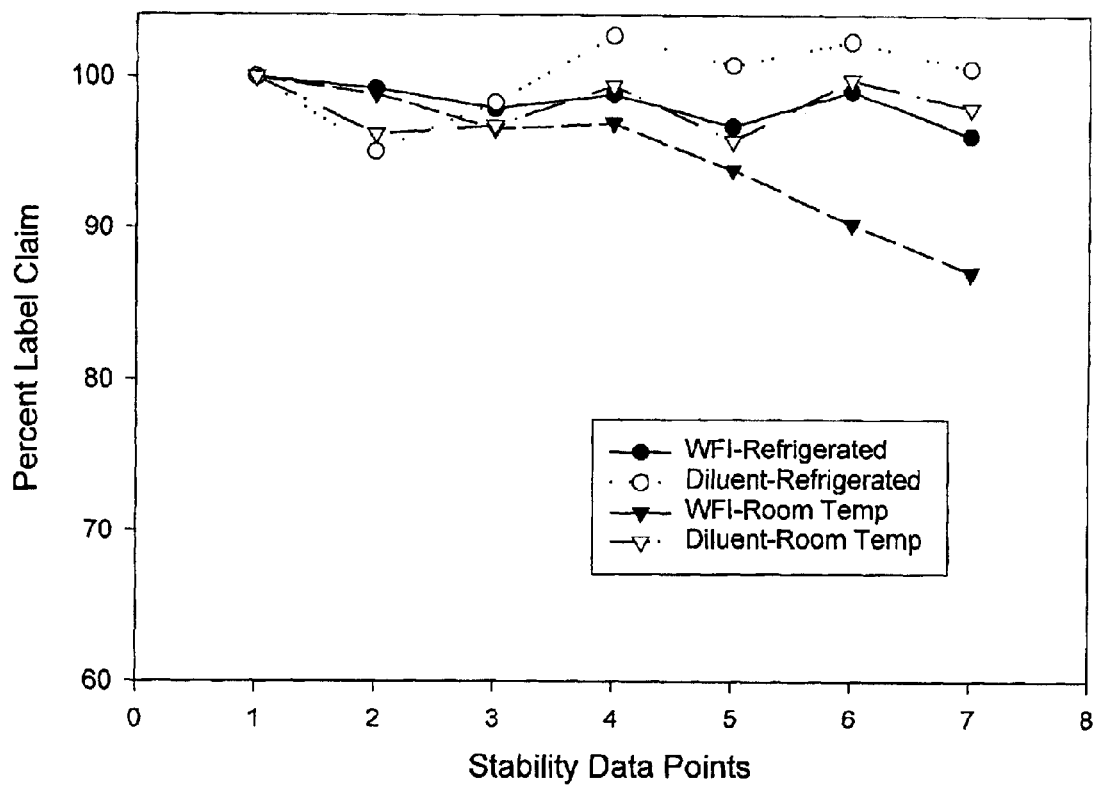
FIG. 3 is a graph representing the stability of two ICG formulations, one comprising ICG and WFI and the other a preferred ICG formulation of the present invention.

Flow rate was 1 ml/min, column temperature was ambient, and detection was at 254 nm. Under these separation conditions, ICG elutes at about 14–15 min. Stability data for a 5 mg/ml ICG formulation is set forth in FIG. 3. Reconstituted ICG (at 5 mg/ml) in the inventive diluent described in Example 1 exhibited stability superior relative to ICG reconstituted in WFI at the same concentration, when stored at room temperature (25° C.) and under refrigerated conditions (4–8° C.).

Microbiological Stability

The bioburden for 25 mg/ml samples prepared by dissolving 25 mg lyophilized ICG in 1 ml of the diluent of Example 1 was tested as set forth in USP.

| Time | Results |
|---|---|
| 0 | 0 cfu |
| 7 days (25° C.) | 0 cfu |
| 7 days (4–8° C.) | 0 cfu |

Viscosity Evaluation

The viscosity of formulations provided in Comparative Example A (ICG with WFI only) was very high; a paste-like consistency. In contrast, the formulations of Examples 1 and 2, at 50 mg/ml and 75 mg/ml ICG, are easy to reconstitute and withdraw from the vial using a syringe, permitting parenteral administration to an animal.

TABLE I

Viscosity (cp at 25° C.) of ICG Compositions Stored in a 25° C. Environment

| Time | 25 mg/ml ICG in Water | 25 mg ICG/ml in Example 1 Diluent | 75 mg/ml ICG in Water | 75 mg ICG/ml in Example 1 Diluent |
|---|---|---|---|---|
| 0 | 0.69 | 1.64 | 19.85 | 2.52 |
| 4 days | 0.69 | 1.37 | 15.4 | 2.29 |
| 1 month | 1.11 | 1.74 | 11.55 | 2.49 |

Fluorescence Evaluation

Figure 2:
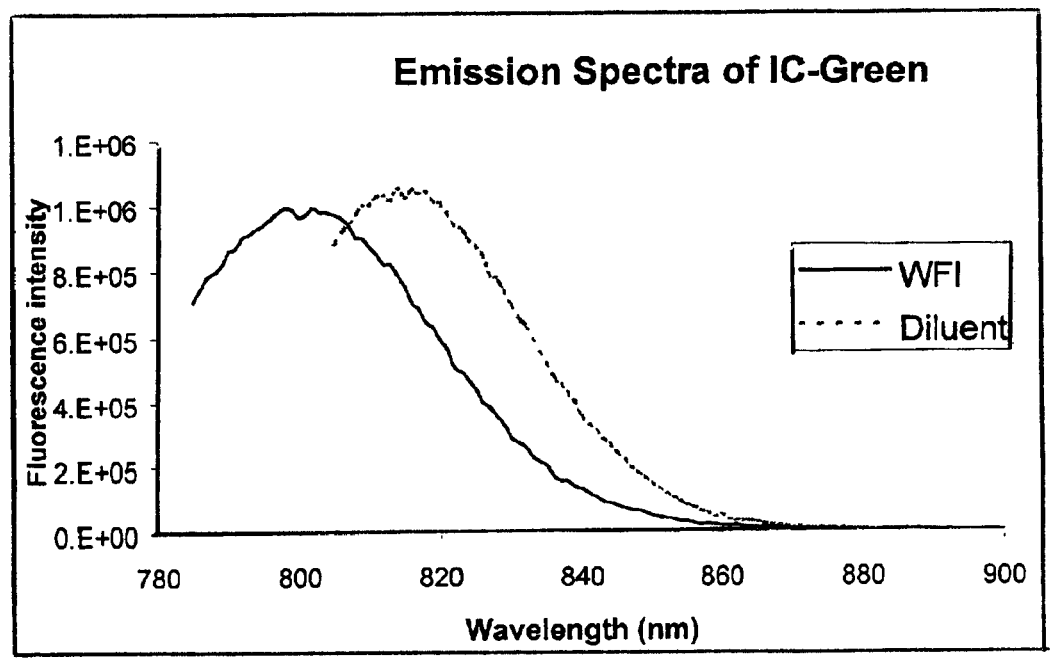
FIG. 2 is an emission spectra of a preferred ICG formulation of the present invention.

The fluorescence of the formulation in Comparative Example A was compared to that of the formulation in Example 1, using equal concentrations of ICG. Fluorescent spectra was recorded using a FluoroMax-2 (Instruments S.A., Inc.), Cuvette (1 cm lightpath), with an excitation spectra of 500–820 nm. The monchromater was set at 830 nm, slit 5 nm. The fluorescence of respective solvents was subtracted as background. The results (see FIG. 1) demonstrate excitation fluorescence that is markedly different for ICG in WFI and ICG in the diluent, the latter over about twice greater. In addition, the excitation maximum in the latter composition is slightly shifted to longer wavelengths. For emission spectra, the ICG/WFI composition was excited at 780 nm, and the ICG/diluent composition was excited at 800 nm. The emission spectra (See FIG. 2) did not show a marked difference in emission intensity. However, there was a shift in emission maxima. This shift in wavelength for emission spectra and increased excitation intensity in the inventive diluent is believed to be indicative of the difference environment surrounding the ICG molecules in solution. It may also indicate the possible interaction between ICG molecules and different components of the diluent, e.g., alcohol, PVP. These interactions are believed to stabilize the ICG, and provide for enhanced stability in an aqueous environment.

X-Ray Diffraction Analysis of Lyophilized ICG

Figure 4:
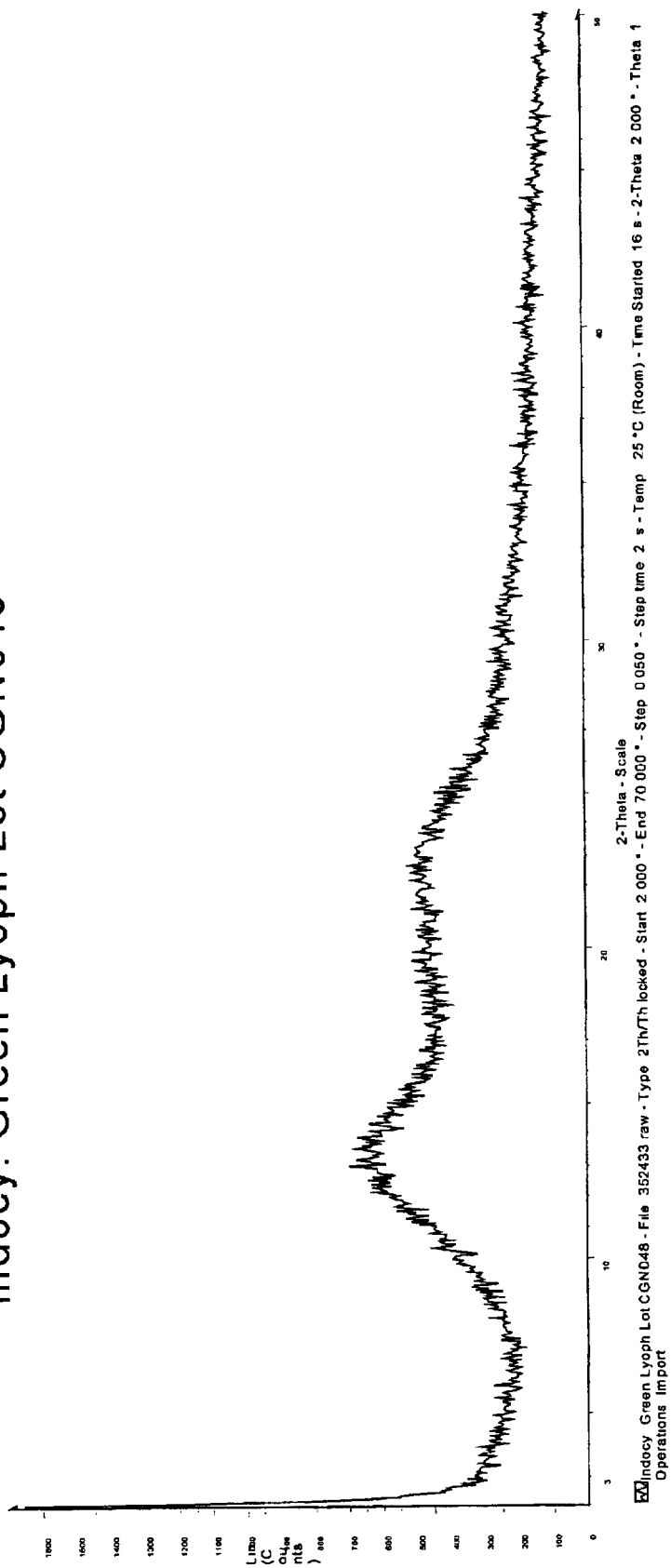
FIG. 4 is X-ray diffraction data for a lyophilized form of ICG.

X-ray diffraction was conducted using Cu Kα radiation from 2 to 70°2θ, an accelerating voltage of 40 kV/30 mA, step size of 0.05° and an acquisition time of 2 seconds per step, with the sample spinning. FIG. 4 shows the resulting scan for the range 2 through 50° for the lyophilized material. The scan indicates that the material is amorphous and is characterized by two very broad humps centered at about 13° and 23° respectively. The lyophilized material is amorphous and hence relatively easily hydrated. The solubility of lyophilized material in WFI and the inventive diluent is comparable up to 25 mg/ml, wherein the inventive diluent is superior at concentrations above that level.

X-Ray Diffraction Analysis of Crystalline ICG

Figure 5:
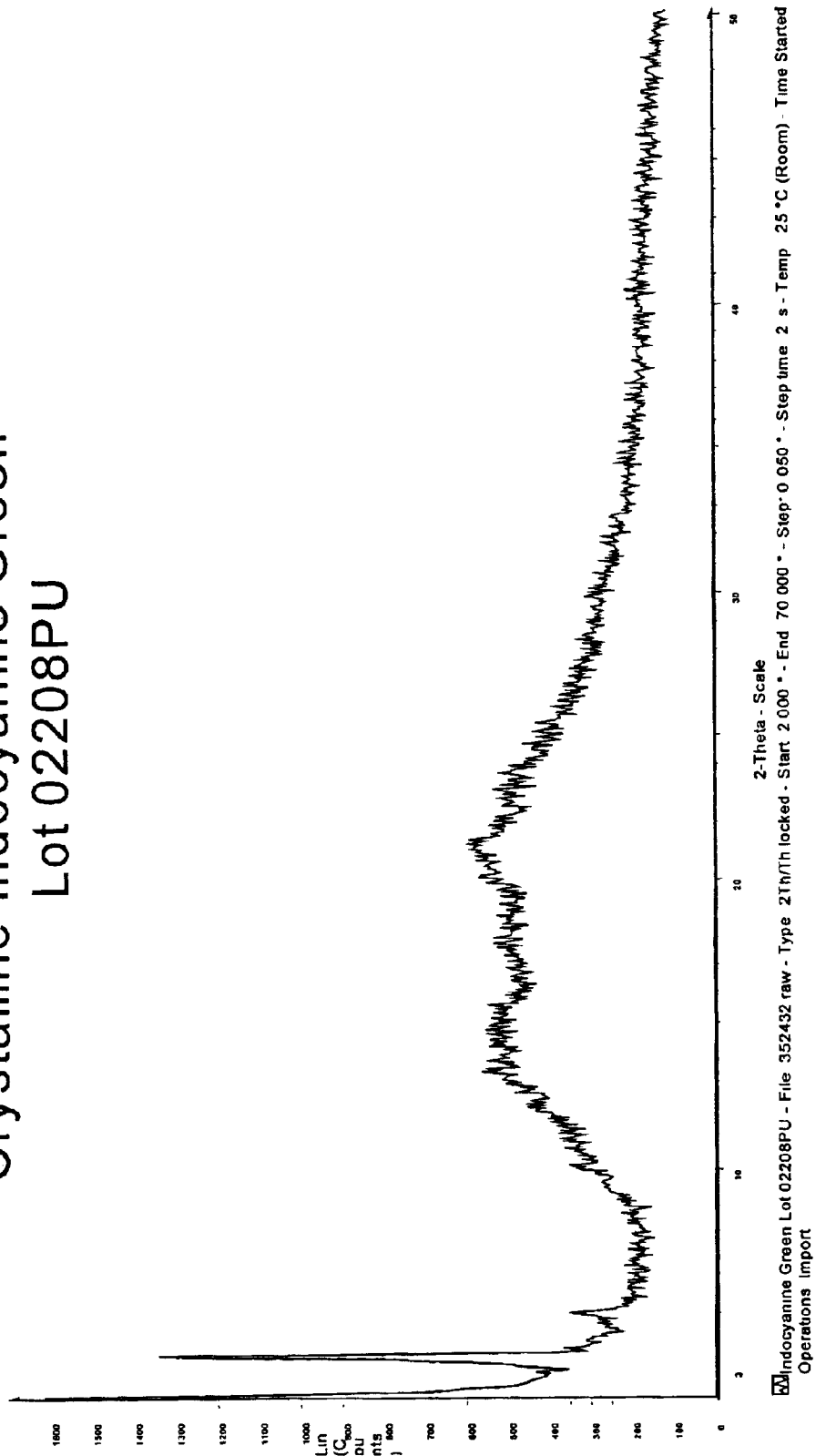
FIG. 5 is X-ray diffraction data for a crystalline form of ICG.

The crystalline material also has a substantial amorphous component, as observed from the broad hump of intensity in FIG. 5. The pattern for this material shows, however, several peaks in the low angle region of the pattern, notably those with d-spacings of 25.8 and 17.9 Å. There is thus some degree of crystallinity observed using this analytical method. This mixed nature of non-lyophilized material results in its low solubility in WFI. The inventive diluent, however, overcomes this relatively low water solubility, and also provides the option of utilizing sterile crystalline powder for ICG-related use. The crystalline ICG is sterilized by gamma radiation or ethylene oxide sterilization techniques, with the sterile powder being filled into vials.

The inventive formulation of Example 1 is thus capable of providing enhanced therapeutic outcomes in both the diagnosis and treatment of an ailment compared to conventional ICG formulations.

EXAMPLE 5

Rat Safety Study

The ICG commercial formulation described in Comparative Example A (5 mg/ml) was tested against the formulation described in Example 2 for safety parameters. A total dose of each formulation was injected into rats at 17.5 mg/kg body weight. Thus, the volume of solution for the 5 mg/ml was 3.5 ml/kg, while for the 75 mg/ml was 0.23 ml/kg. The results of these injections are set forth below.

TABLE 1

Mean Body Weights (g) - Males

| Group | | Pretest Day 1 | Dosing | Week 1 | Week 2 |
|---|---|---|---|---|---|
| Comparative | Mean | 255.4 | 264.8 | 307.6 | 345.2 |
| Example A | Std. Dev. | 6.47 | 4.97 | 7.23 | 9.04 |
| Formulation | (n) | (5) | (5) | (5) | (5) |
| Example 2 | Mean | 251.2 | 258.4 | 298.6 | 339.0 |
| Formulation | Std. Dev. | 6.30 | 4.83 | 11.68 | 13.21 |
| | (n) | (5) | (5) | (5) | (5) |

TABLE 2

Mean Body Weights (g) - Females

| Group | | Pretest Day 1 | Dosing | Week 1 | Week 2 |
|---|---|---|---|---|---|
| Comparative | Mean | 200.8 | 208.4 | 227.4 | 244.0 |
| Example A | Std. Dev. | 8.61 | 8.05 | 9.13 | 13.51 |
| Formulation | (n) | (5) | (5) | (5) | (5) |
| Example 2 | Mean | 198.4 | 203.4 | 223.2 | 238.0 |
| Formulation | Std. Dev. | 126.7 | 6.58 | 5.07 | 8.28 |
| | (n) | (5) | (5) | (5) | (5) |

TABLE 3

Mean Hematology Data - Males

| Group (mg/kg/day) | | WBC $10^3/mm^3$ | RBC $10^6/mm^3$ | HGB g/dL | HCT % | MCV fL | MCH pg | MCHC g/dL | PLT $10^3/mm^3$ | PT sec |
|---|---|---|---|---|---|---|---|---|---|---|
| Comparative | Mean | 8.88 | 6.53 | 14.8 | 40.6 | 62.1 | 22.6 | 36.3 | 948 | 17.8 |
| Example A | Std. Dev. | 4.516 | 0.376 | 1.18 | 2.90 | 1.39 | 0.77 | 0.73 | 491.2 | 0.71 |
| Formulation | (n) | (5) | (5) | (5) | (5) | (5) | (5) | (5) | (5) | (5) |
| Example 2 | Mean | 13.3 | 6.55 | 14.7 | 40.0 | 61.1 | 22.5 | 36.9 | 1166 | 18.1 |
| Formulation | Std. Dev. | 4.637 | 0.194 | 0.45 | 1.82 | 4.31 | 1.21 | 0.70 | 378.6 | 1.12 |
| | (n) | (5) | (5) | (5) | (5) | (5) | (5) | (5) | (5) | (5) |

TABLE 4

Mean Hematology Data - Females

| Group (mg/kg/day) | | WBC $10^3/mm^3$ | RBC $10^6/mm^3$ | HGB g/dL | HCT % | MCV fL | MCH pg | MCHC g/dL | PLT $10^3/mm^3$ | PT sec |
|---|---|---|---|---|---|---|---|---|---|---|
| Comparative | Mean | 10.36 | 6.61 | 14.8 | 42.6 | 64.5 | 22.3 | 34.7 | 1241 | 18.0 |
| Example A | Std. Dev. | 0.983 | 0.337 | 0.59 | 1.79 | 1.72 | 0.80 | 0.46 | 117.6 | 0.39 |
| Formulation | (n) | (5) | (5) | (5) | (5) | (5) | (5) | (5) | (5) | (5) |
| Example 2 | Mean | 10.04 | 6.62 | 14.7 | 42.2 | 63.8 | 22.3 | 34.9 | 1020 | 17.7 |
| Formulation | Std. Dev. | 2.457 | 0.089 | 0.33 | 1.18 | 1.64 | 0.43 | 0.36 | 252.1 | 0.81 |
| | (n) | (5) | (5) | (5) | (5) | (5) | (5) | (5) | (5) | (5) |

Key to Hematology Abbreviations

| Abbreviation | Parameter |
|---|---|
| Hematological Values: | |
| RBC | Erythrocyte Count |
| HGB | Hemoglobin concentration |
| HCT | Hematocrit |
| MCV | Mean Corpuscular Volume |
| MCH | Mean Corpuscular Hemoglobin |
| MCHC | Mean Corpuscular Hemoglobin Concentration |
| PLT | Platelet Count |
| WBC | Total Leukocyte Count |
| PT | Prothrombin Time |

TABLE 5

Mean Clinical Chemistry - Males

| Group | | BUN mg/dL | CREAT mg/dL | ALT U/L | AST U/L | ALP U/L | T BILI mg/dL | T PRO G/dL | ALB g/dL | GLOB g/dL | AG Ratio |
|---|---|---|---|---|---|---|---|---|---|---|---|
| Comparative | Mean | 17.4 | 0.58 | 50.8 | 130.4 | 439.8 | 0.42 | 5.80 | 3.58 | 2.22 | 1.61 |
| Example A | Std. Dev. | 0.55 | 0.045 | 3.03 | 12.54 | 106.68 | 0.045 | 0.224 | 0.130 | 0.110 | 0.053 |
| Formulation | (n) | (5) | (5) | (5) | (5) | (5) | (5) | (5) | (5) | (5) | (5) |
| Example 2 | Mean | 19.6 | 0.64 | 58.4 | 124.2 | 492.6 | 0.48 | 5.88 | 3.56 | 2.32 | 1.54 |
| Formulation | Std. Dev. | 2.51 | 0.055 | 13.69 | 6.06 | 199.20 | 0.164 | 0.148 | 0.167 | 0.164 | 0.166 |
| | (n) | (5) | (5) | (5) | (5) | (5) | (5) | (5) | (5) | (5) | (5) |

| Group | | GLU mg/dL | NA mEq/L | K mEq/L | CL mEq/L | CA mg/dL | I PHOS mg/dL | CREAT K U/L | CHOL mg/dL | GGT U/L | TRI-G |
|---|---|---|---|---|---|---|---|---|---|---|---|
| Comparative | Mean | 144.8 | 146.9 | 6.1 | 104.8[B] | 9.9 | 8.2 | 771 | 66.6 | 0.02 | 133.2 |
| Example A | Std. Dev. | 6.72 | 1.05 | 0.23 | 1.48 | 0.25 | 0.42 | 257.6 | 7.64 | 0.04 | 16.84 |
| Formulation | (n) | (5) | (5) | (5) | (5) | (5) | (5) | (5) | (5) | (5) | (5) |
| Example 2 | Mean | 146.6 | 146.2 | 5.9 | 106.0 | 10.0 | 8.8 | 581 | 63.4 | 0.10 | 151.8 |
| Formulation | Std. Dev. | 7.16 | 3.02 | 0.48 | 1.58 | 0.16 | 0.46 | 180.9 | 8.64 | 0.14 | 58.84 |
| | (n) | (5) | (5) | (5) | (5) | (5) | (5) | (5) | (5) | (5) | (5) |

Mean Clinical Chemistry - Females

| Group | | BUN mg/dL | CREAT mg/dL | ALT U/L | AST U/L | ALP U/L | T BILI mg/dL | T PRO G/dL | ALB g/dL | GLOB g/dL | AG Ratio |
|---|---|---|---|---|---|---|---|---|---|---|---|
| Comparative | Mean | 19.4 | 0.74 | 49.6 | 122.4 | 260.0 | 0.30 | 6.06 | 3.92 | 2.14 | 1.84 |
| Example A | Std. Dev. | 1.50 | 0.558 | 5.60 | 25.23 | 35.56 | 0.123 | 0.195 | 0.130 | 0.114 | 0.103 |
| Formulation | (n) | (5) | (5) | (5) | (5) | (5) | (5) | (5) | (5) | (5) | (5) |

TABLE 5-continued

| | | | | | | | | | | |
|---|---|---|---|---|---|---|---|---|---|---|
| Example 2 | Mean | 19.4 | 0.68 | 58.2 | 123.4 | 257.0 | 0.44 | 5.92^A | 3.80 | 2.12 | 1.80 |
| Formulation | Std. Dev. | 1.50 | 0.110 | 12.64 | 24.28 | 44.23 | 0.114 | 0.164 | 0.123 | 0.148 | 0.157 |
| | (n) | (5) | (5) | (5) | (5) | (5) | (5) | (5) | (5) | (5) | (5) |

| Group | | GLU mg/dL | NA mEq/L | K mEq/L | CL mEq/L | CA mg/dL | I PHOS mg/dL | CREAT K U/L | CHOL mg/dL | GGT U/L | TRI-G |
|---|---|---|---|---|---|---|---|---|---|---|---|
| Comparative | Mean | 167.6 | 143.5 | 5.0 | 108.4^A | 10.2 | 6.8 | 586 | 69.0 | 0.08 | 76.0 |
| Example A | Std. Dev. | 7.37 | 1.87 | 0.34 | 2.30 | 0.43 | 0.58 | 328.2 | 10.65 | 0.13 | 5.15 |
| Formulation | (n) | (5) | (5) | (5) | (5) | (5) | (5) | (5) | (5) | (5) | (5) |
| Example 2 | Mean | 174.4 | 146.3 | 4.9 | 108.8 | 10.1 | 7.1 | 512 | 71.2 | 0.12 | 106.4 |
| Formulation | Std. Dev. | 10.78 | 3.47 | 0.50 | 1.94 | 0.30 | 0.49 | 168.0 | 6.91 | 0.18 | 39.15 |
| | (n) | (5) | (5) | (5) | (5) | (5) | (5) | (5) | (5) | (5) | (5) |

Key to Clinical Chemistry Abbreviations

| Abbreviation | Parameter | Abbreviation | Parameter |
|---|---|---|---|
| BUN | Blood Urea Nitrogen | GLU | Glucose |
| CREAT | Creatinine | NA | Sodium |
| ALT | Alanine Aminotransferase | K | Potassium |
| AST | Aspartate Aminotransferase | CL | Chloride |
| ALP | Alkaline Phosphatase | CA | Calcium |
| T BILI | Total Bilirubin | I PHOS | Inorganic Phosphorus |
| T PRO | Total Protein | CREAT K | Creatine Kinase |
| ALB | Albumin | CHOL | Cholesterol |
| GLOB | Globulin | GGT | γ-glutamyltransferase |
| AG Ratio | Albumin/Globulin Ratio (calculated) | | |
| TRI-G | Triglycerides | | |

The animals were observed at 1, 2.5 and 4 hours after injection, and daily for 14 days. On day 13, blood was taken for hematology and clinical chemistry determinations. Neither formulation caused any mortality nor change in blood chemistry and hematology.

The animals were necropsied on day 14 and all tissues were examined by a pathologist. The histopathology of the tissues were found to be normal.

All of the references cited herein, including patents, patent applications, and publications, are hereby incorporated in their entireties by reference. Further, and unless otherwise indicated, references to a single component or step should be construed as also including more than one component or step, i.e., at least one. Moreover, the various components and associated numerical ranges may be included and used in the inventive compositions independent of one another and also of the other components.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

We claim:

1. An aqueous indocyanine green (ICG) composition comprising ICG at a concentration of at least about 20 mg/ml and an aqueous diluent comprising a solubilizer and an alcohol, wherein the composition exhibits a loss of ICG potency of less than about 10% for at least 24 hours when stored in a 25° C. environment.

2. The aqueous ICG composition according to claim 1, wherein the composition exhibits a loss of ICG potency of less than about 10% for at least 48 hours.

3. The aqueous ICG composition according to claim 2, wherein the composition exhibits a loss of ICG potency of less than about 10% for at least 5 days.

4. The aqueous ICG composition according to claim 1, wherein the ICG concentration is at least about 50 mg/ml.

5. The aqueous ICG composition according to claim 4, wherein the composition exhibits a loss of ICG potency of less than about 10% for at least 5 days.

6. The aqueous ICG composition according to claim 5, wherein the composition exhibits a loss of ICG potency of less than about 10% for at least one week.

7. The aqueous ICG composition according to claim 4, wherein the ICG concentration is at least about 75 mg/ml.

8. The aqueous ICG composition according to claim 7, wherein the composition exhibits a loss of ICG potency of less than about 10% for at least 24 hours.

9. The aqueous ICG composition according to claim 8, wherein the composition exhibits a loss of ICG potency of less than about 10% for at least three days.

10. The aqueous ICG composition according to claim 9, wherein the composition exhibits a loss of ICG potency of less than about 10% for at least one week.

11. The composition according to claim 4, wherein the ICG composition comprises no more than about 1 wt. % degradation product when stored in the 25° C. environment.

12. The aqueous ICG composition according to claim 1, wherein the aqueous diluent comprises, per ml of diluent, about 0.5 to about 5 mg solubilizer and about 50 to about 150 mg alcohol, and wherein the composition has a pH of about 6 to about 8.

13. The aqueous ICG composition according to claim 12, wherein the solubilizer is a surfactant.

14. The aqueous ICG composition according to claim 13, wherein the alcohol is ethanol, propylene glycol, glycerine, or mixtures thereof.

15. The aqueous ICG composition according to claim 14, wherein the solubilizer is a nonionic surfactant.

16. The aqueous ICG composition according to claim 12, wherein the aqueous diluent further comprises, per ml of diluent, about 10 to about 100 mg polyvinyl pyrrolidone.

17. The aqueous ICG composition according to claim 16, wherein the aqueous diluent further comprises an antimicrobial in an amount effective to inhibit microbial growth in the aqueous ICG composition for at least one week.

18. The aqueous ICG composition according to claim 17, wherein the aqueous diluent comprises, per ml of diluent, about 1 to about 3 mg surfactant, about 75 to about 125 mg alcohol, about 25 to about 75 mg PVP, and wherein the pH of the diluent is about 6.5 to about 7.5.

19. The composition according to claim 18, wherein the ICG composition comprises no more than about 1 wt. % degradation product when stored in the 25° C. environment.

20. The aqueous ICG composition according to claim 12, wherein the ICG and aqueous diluent are segregated within a multi-chambered vessel prior to formation of the aqueous ICG composition.

21. The aqueous ICG composition according to claim 20, wherein the multi-chambered vessel is a dual-chamber syringe.

22. The aqueous ICG composition according to claim 20, wherein the multi-chambered vessel is a vial.

23. The composition according to claim 12, wherein the ICG composition comprises no more than about 1 wt. % degradation product when stored in the 25° C. environment.

24. The aqueous ICG composition according to claim 1, wherein the ICG is provided as a sterile lyophilizate.

25. The aqueous ICG composition according to claim 24, wherein the composition is a liposomal ICG composition.

26. The composition according to claim 1, wherein the ICG composition comprises no more than about 1 wt. % degradation product when stored in the 25° C. environment.

27. A method for providing an aqueous indocyanine green (ICG) composition comprising diluting ICG with art aqueous diluent comprising a solubilizer and an alcohol to provide an aqueous composition of ICG at a concentration of at least 20 mg/ml, wherein the aqueous ICG composition exhibits a loss of ICG potency of less than about 10% for at least 24 hours when stored in a 25° C. environment.

28. The method according to claim 27, wherein the ICG is lyophilized prior to dilution with the aqueous diluent.

29. The method according to claim 27, wherein the ICG and aqueous diluent are segregated within a multi-chambered vessel prior to diluting the ICG with the aqueous diluent.

30. The method according to claim 29, wherein the multi-chambered vessel is a dual-chamber syringe.

31. The method according to claim 29, wherein the multi-chambered vessel is a vial.

32. The method according to claim 27, wherein the composition exhibits a loss of ICG potency of less than about 10% for at least 48 hours.

33. The method according to claim 32, wherein the composition exhibits a loss of ICG potency of less than about 10% for at least 5 days.

34. The method according to claim 27, wherein the ICG concentration is at least about 50 mg/ml.

35. The method according to claim 34, wherein the composition exhibits a loss of ICG potency of less than about 10% for at least 5 days.

36. The method according to claim 35, wherein the composition exhibits a loss of ICG potency of less than about 10% for at least one week.

37. The method according to claim 34, wherein the ICG concentration is at least about 75 mg/ml.

38. The method according to claim 37, wherein the composition exhibits a loss of ICG potency of less than about 10% for at least 24 hours.

39. The method according to claim 38, wherein the composition exhibits a loss of ICG potency of less than about 10% for at least three days.

40. The method according to claim 39, wherein the composition exhibits a loss of ICG potency of less than about 10% for at least one week.

41. The method according to claim 27, wherein the aqueous diluent comprises, per ml of diluent, about 0.5 to about 5 mg solubilizer and about 50 to about 150 mg alcohol, and wherein the composition has a pH of about 6 to about 8.

42. The method according to claim 41, wherein the solubilizer is a surfactant.

43. The method according to claim 42, wherein the alcohol is ethanol, propylene glycol, glycerine, or mixtures thereof.

44. The method according to claim 43, wherein the solubilizer is a nonionic surfactant.

45. The method according to claim 41, wherein the aqueous diluent further comprises, per ml of diluent, about 10 to about 100 polyvinyl pyrrolidone.

46. The method according to claim 45, wherein the aqueous diluent further comprises an antimicrobial in an amount effect to inhibit microbial growth in the aqueous ICG composition for least 7 days.

47. The method according to claim 46, wherein the aqueous diluent comprises, per ml of diluent, about 1 to about 3 mg surfactant, about 75 to about 125 mg alcohol, about 25 to about 75 mg PVP, and wherein the pH of the diluent is about 6.5 to about 7.5.

48. The method according to claim 27, wherein the ICG is provided as a lyophilizate.

49. The method according to claim 48, wherein the lyophilizate further comprises components which, when water is added, provide liposomal ICG.

50. A multi-chambered vessel comprising indocyanine green (ICG) is a first chamber and an aqueous diluent comprising a solubilizer and an alcohol in a second chamber, wherein the diluent, when mixed with the ICG, provides an aqueous composition having an ICG concentration of at least 20 mg/ml and exhibits composition having an ICG concentration of at least 20 mg/ml and exhibits a loss of ICG potency of less than about 10% for at least 24 hours when stored in a 25° C. environment.

51. The multi-chambered vessel according to claim 50, wherein the vessel is a dual-chamber syringe.

52. The multi-chambered vessel according to claim 51, wherein the first chamber of the syringe comprises ICG as a lyophilizate.

53. The multi-chambered vessel according to claim 51, wherein the multi-chambered vessel is a vial.

54. A method of obtaining an angiographic image of tissue in a patient comprising administering an aqueous ICG composition comprising ICG at a concentration of at least about 20 mg/ml and an aqueous diluent comprising a solubilizer and an alcohol to a patient; applying energy of a type and in an amount sufficient to cause ICG in the patient to fluoresce; and obtaining an angiographic image of the tissue while the ICG fluoresces, wherein the aqueous ICG composition exhibits a loss of ICG potency of less than about 10% for at least 24 hours when stored in a 25° C. environment.

55. The method of claim 54, wherein the energy is administered using an endoscope.

56. The method of claim 55, wherein the tissue is the eye, lung, gastrointestinal tract, bladder, pancreas, gall bladder, sinus, trachea, liver, kidney, heart, cervix, brain, ovary, prostate, stomach or skin.

57. The method according to claim 55, wherein the ICG is in the aqueous ICG composition at a concentration of at least 75 mg/ml.

58. The method according to claim 57, wherein the aqueous composition exhibits a loss of ICG potency of less than about 10% for at least 48 hours.

59. The method according to claim 57, wherein the aqueous composition exhibits a loss of ICG potency of less than about 10% for at least 7 days.

60. The method of claim 54, wherein the angiographic image is of tissue that defines a body cavity.

61. The method according to claim 54, wherein the ICG is in the aqueous ICG composition at a concentration of at least 50 mg/ml.

62. The method according to claim 61, wherein the aqueous composition exhibits a loss of ICG potency of less than about 10% for at least 48 hours.

63. The method according to claim 62, wherein the aqueous composition exhibits a loss of ICG potency of less than about 10% for at least 7 days.

64. The method according to claim 54, further comprising applying radiation of a type and in an amount effective to provide photodynamic therapy to the patient.

65. The method according to claim 64, wherein the radiation effective to provide photodynamic therapy is administered by an endoscope.

66. The method according to claim 65, wherein the ICG is provided at a concentration of at least 25 mg/ml.

67. The method according to claim 66, wherein the ICG is provided at a concentration of at least 50 mg/ml.

68. A method for diagnosing and treating a lesion in an animal, wherein a blood vessel feeds blood into the lesion, comprising
   (a) administering an aqueous ICG composition comprising ICG at a concentration of at least about 25 mg/ml and an aqueous diluent comprising a solubilizer and an alcohol to a patient;
   (b) applying energy of a type and in an amount sufficient to cause the ICG to fluoresce as the ICG flows through the blood vessels;
   (c) obtaining an angiographic image of the fluorescing ICG dye as the dye flows through the blood vessels;
   (d) analyzing the angiographic image obtained in step (c) to determine the presence of a lesion; and
   (e) applying energy to the blood vessel feeding blood into the lesion of a type and in an amount sufficient to reduce the rate of rate of blood flow through the blood vessel, wherein the aqueous ICG composition exhibit a loss of ICG potency of less than about 10% for at least 24 hours when stored in a 25° C. environment.

69. The method of claim 68, wherein the energy is administered using an endoscope.

70. The method of claim 68, wherein the angiographic image is of tissue that defines a body cavity.

71. The method of claim 70, wherein the tissue is the eye, lung, gastrointestinal tract, bladder, pancreas, gall bladder, sinus, trachea, liver, kidney, heart, cervix, brain, ovary, prostate, stomach or skin.

72. The method according to claim 68, wherein the ICG is in the aqueous ICG composition at a concentration of at least 50 mg/ml.

73. The method according to claim 72, wherein the aqueous composition exhibits a loss of ICG potency of less than about 10% for at least 48 hours.

74. The method according to claim 73, wherein the aqueous composition exhibits a loss of ICG potency of less than about 10% for at least 7 days.

75. The method according to claim 68, wherein the ICG is in the aqueous ICG composition at a concentration of at least 75 mg/ml.

76. The method according to claim 75, wherein the aqueous composition exhibits a loss of ICG potency of less than about 10% for at least 48 hours.

77. The method according to claim 76, wherein the aqueous composition exhibits a loss of ICG potency of less than about 10% for at least 7 days.

78. The method according to claim 68, further comprising applying radiation of a type and in an amount effective to provide photodynamic therapy to the patient.

79. The method according to claim 78, wherein the radiation effective to provide photodynamic therapy is administered by an endoscope.

80. The method according to claim 79, wherein the ICG is provided at a concentration of at least 50 mg/ml.

81. The method according to claim 78, wherein step (e) comprises applying radiation of a type and in an amount sufficient to provide dye-enhanced photocoagulation as the dye enters the targeted tissue, and subsequently applying radiation of a type and in an amount to provide for PDT.

82. A method for reducing the rate of blood flow through a vessel that carries blood into a tumor of an animal comprising
   (a) administering an aqueous ICG composition comprising ICG at a concentration of at least about 20 mg/ml and an aqueous diluent comprising a solubilizer and an alcohol to a patient; and
   (b) after the ICG dye enters the blood vessel that carries blood into the tumor, applying energy to the blood vessel of a type and in an amount sufficient to excite the ICG in the blood vessel and reduce the rate of blood flow through the vessel, wherein the ICG composition exhibits a loss of ICG potency of less than about 10% for at least 24 hours when stored in a 25° C. environment.

83. The method according to claim 82, wherein step (b) comprises applying radiation as the dye entered the vessel of a type and in an amount sufficient to provide dye-enhanced photocoagulation of the vessel, and further comprising applying radiation to the tumor of a type and in an amount to provide PDT to the tumor.

84. The method of claim 83, wherein the angiographic image is of tissue that defines a body cavity.

85. The method of claim 84, wherein the tissue is the eye, lung, gastrointestinal tract, bladder, pancreas, gall bladder, sinus, liver, trachea, kidney, heart, cervix, brain, ovary, prostate, stomach or skin.

86. The method according to claim 85, wherein the radiation effective to provide photodynamic therapy is administered by an endoscope.

87. The method according to claim 86, wherein the ICG is provided at a concentration of at least 25 mg/ml.

88. The method according to claim 86, where n the ICG is provided at a concentration of at least 50 mg/ml.

89. The method according to claim 85, wherein the radiation effective to provide photodynamic therapy is administered by an endoscope.

90. The method according to claim 83, further comprising applying radiation of a type and in an amount effective to provide photodynamic therapy to the patient.

91. The method according to claim 83, wherein the ICG is in the aqueous ICG composition at a concentration of at least 50 mg/ml.

92. The method according to claim 91, wherein the aqueous composition exhibits a loss of ICG potency of less than about 10% for at least 48 hours.

93. The method according to claim 92, wherein the aqueous composition exhibits a loss of ICG potency of less than about 10% for at least 7 days.

94. The method of claim 82, wherein the radiation is administered in at least step (b) using an endoscope.

95. The method according to claim 94, wherein the ICG is in the aqueous ICG composition at a concentration of at least 75 mg/ml.

96. The method according to claim 95, wherein the aqueous composition exhibits a loss of ICG potency of less than about 10% for at least 48 hours.

97. The method according to claim 96, wherein the aqueous composition exhibits a loss of ICG potency of less than about 10% for at least 7 days.

* * * * *

UNITED STATES PATENT AND TRADEMARK OFFICE
CERTIFICATE OF CORRECTION

PATENT NO. : 6,944,493 B2
DATED : September 26, 2006
INVENTOR(S) : Alam et al.

It is certified that error appears in the above-identified patent and that said Letters Patent is hereby corrected as shown below:

Title page,
Item [73], Assignee, reads, "Akora, Inc.," should read -- Akorn, Inc. --.

Signed and Sealed this

Fifteenth Day of November, 2005

JON W. DUDAS
*Director of the United States Patent and Trademark Office*